(12) United States Patent
Franke

(10) Patent No.: US 6,237,431 B1
(45) Date of Patent: May 29, 2001

(54) APPARATUS FOR TESTING HOLLOW BODIES FOR DEFECTS

(75) Inventor: Reiner Franke, Mönchengladbach (DE)

(73) Assignee: Reiner Franke GmbH & Co. Glasbautechnikmaschinen KG (DE)

( * ) Notice: Subject to any disclaimer, the term of this patent is extended or adjusted under 35 U.S.C. 154(b) by 0 days.

(21) Appl. No.: 09/181,347

(22) Filed: Oct. 28, 1998

(30) Foreign Application Priority Data

Oct. 30, 1997 (DE) .............................................. 297 19 303
Sep. 1, 1998 (DE) .............................................. 198 39 746

(51) Int. Cl.[7] .................................................. G01M 19/00
(52) U.S. Cl. ............................ 73/865.8; 73/52; 356/428; 356/240.1
(58) Field of Search .................... 73/865.8, 52; 356/428, 356/240.1

(56) References Cited

U.S. PATENT DOCUMENTS

| | | | |
|---|---|---|---|
| 3,944,058 | * | 3/1976 | Strauss ................................... 198/179 |
| 4,208,130 | * | 6/1980 | Saconney et al. .................... 356/428 |
| 4,323,158 | * | 4/1982 | Wheaton, III et al. .............. 356/428 |
| 4,790,662 | * | 12/1988 | Bischkopf et al. ................... 356/428 |
| 4,863,275 | * | 9/1989 | Cormack et al. ..................... 356/428 |
| 5,719,679 | * | 2/1998 | Shimizu et al. ...................... 356/428 |

* cited by examiner

Primary Examiner—Hezron Williams
Assistant Examiner—Michael Cygan
(74) Attorney, Agent, or Firm—Mason, Kolehmainen, Rathburn & Wyss

(57) ABSTRACT

Apparatus for testing non-rotationally symmetrical hollow bodies for defects includes a conveyor for continuously conveying the hollow body through a test region past a detector for producing measurement values characterising the nature of the respective hollow bodies being tested, in dependence on the angle of rotation of the hollow body. An evaluator device compares the measurement values to predetermined values to decide whether the respective hollow body being tested suffers from defects. The conveyor has a receiving device which is fitted over the respective hollow body to embrace it. The receiving device with the hollow body is rotated through a predetermined angular amount while the hollow body is being transported past the detector device. The receiving device is removed from the hollow body again in the region where the conveyor conveys the hollow bodies out of the test region.

7 Claims, 5 Drawing Sheets

SEE Fig. 2

APPARATUS FOR TESTING HOLLOW BODIES FOR DEFECTS

FIELD OF THE INVENTION

The invention concerns an apparatus for testing hollow bodies for defects, more particularly non-rotationally symmetrical hollow bodies.

It will be noted at this stage that the hollow bodies to be tested are preferably non-rotationally symmetrical glass bodies such as for example wide, rounded bottles which are typically used for containing Franconian wine, rectangular bottles, triangular bottles, medication and drug bottles or non-rotationally symmetrical perfume flacons.

BACKGROUND OF THE INVENTION

A typical form of apparatus for testing non-rotationally symmetrical hollow bodies for defects comprises a feed means for continuously conveying the hollow bodies into a test region of the apparatus, a means for conveying the hollow bodies through the test region of the apparatus, and a discharge means for conveying the hollow bodies out of the test region. Such an apparatus is used when there is a wish to check and inspect glass bodies of the above-indicated kind for surface defects such as for example cracks or irregular wall thicknesses in an automated procedure after production of the glass bodies, and to separate out glass bodies which are found to be defective.

SUMMARY OF THE INVENTION

An object of the present invention is to provide an apparatus for testing non-rotationally symmetrical hollow bodies for defects, which is reliable and flexible in operation and which permits testing of all sides of a respective hollow body at a high rate of operation.

Another object of the present invention is to provide an apparatus for testing non-rotationally symmetrical hollow bodies for defects which readily permits all sides of a hollow body to be accurately checked and tested for defects at a speed of several hollow bodies, typically between one and four bodies, per second.

Still another object of the present invention is to provide an apparatus for testing non-rotationally symmetrical hollow bodies for defects thereof which is so designed that the apparatus can be readily and easily adapted to deal with different types of hollow bodies such as glass bodies.

In accordance with the principles of the present invention, the foregoing and other objects are attained by an apparatus for testing non-rotationally symmetrical hollow bodies for defects, comprising a test region, a feed means for continuously conveying the hollow bodies to be tested into the test region, a means for conveying the hollow bodies through the test region, and means for conveying the hollow bodies out of the test region. Disposed at the test region are detector means for producing measurement values characterising the nature of the hollow body respectively being tested in dependence on an angle of rotation of the hollow body. An evaluation means is operable to compare the detected measurement values to predetermined values to decide whether the hollow body respectively being tested has defects. The means for conveying the hollow bodies through the test region includes a receiving means adapted to embrace the hollow body and a drive means adapted to push the receiving means over the respective hollow body to be tested, which is supplied from said feed means. The receiving means is removed from the tested hollow body again in the region of the discharge means for conveying the hollow bodies out of the test region of the apparatus. As the hollow body is transported through the test region and past the detector means, the receiving means with the hollow body therein is rotated through a predetermined angular distance during the transportation movement past the detector means.

The detector means for example may comprise a device which operates optically. Where the hollow body to be tested is typically a glass body, light is shone through the glass body and the degree of reflection or transmission of the light is measured at a height or a plurality of predetermined heights on the glass body, in dependence on the angle of rotation. When using a detector means of that kind, defective glass bodies can be detected on the basis of a comparison of the angle-dependent reflection or transmission profile of the glass body being tested, with stored reflection or transmission profiles of intact glass bodies. By virtue of the fact that the receiving means is operable to embrace the hollow body, the non-rotationally symmetrical hollow body can be rotated through a defined angular amount by virtue of the rotary movement of the receiving means, whereby it is possible to record a measurement curve which is dependent on the angle of rotation. The hollow bodies are supplied to the test region of the apparatus by the feed means in a defined angular position and, after the rotary movement of the hollow body through a predetermined angle, the hollow bodies are subjected to further conveying movement through the apparatus, in a defined angular position.

A preferred feature of the invention provides that the receiving means is adapted to be easily replaceable and interchangeable so that the apparatus can be rapidly adapted to deal with different hollow body contours and configurations.

In another preferred feature of the invention, the means for conveying the hollow bodies through the test region includes a guidance means having a guide bar portion which is centered with respect to the axis of rotation of the receiving means and which is adapted to be movable up and down in relation thereto. Upon transportation of the hollow body in the test region of the apparatus, the guide bar portion is adapted to be introduced from above into an opening of the hollow body to be tested. The opening may be for example the opening in the neck of a bottle. The action of the guide bar portion co-operating with the hollow body thus prevents the hollow body from falling over during the conveying and rotary movement thereof.

In accordance with a preferred embodiment of the invention, it can further be provided that the receiving means is mounted rotatably about its axis of rotation on a first slide means which is driven by an eccentric arrangement and which performs a stroke movement in a vertical direction and a transportation movement which is transverse with respect thereto. The receiving means has an external tooth configuration which is operatively engaged with a gear driven by a synchronous motor. The first slide means provides for a continuous movement of the receiving means along a substantially elliptical path. The driving eccentric arrangement is preferably mechanically synchronised with the means for feeding the hollow bodies into the test region and for further transporting them therethrough, such means usually comprising conveyor screws. In the phase of engagement of the receiving means, the above-mentioned synchronous motor performs a movement through a predetermined angular amount and produces a corresponding rotary movement of the receiving means. The rotor position of the synchronous motor, which is known to the control system of the apparatus, can be correlated to the angular position of the hollow body, so that it is possible to provide for absolute value detection of the current angular position of the hollow body.

A preferred feature of the invention provides that the synchronous motor is arranged on an element of the first slide means, that is non-participatory in the vertical stroke movement of the receiving means. The rotary movement of the drive shaft of the synchronous motor is transmitted to the gear by way of a shaft of non-rotationally symmetrical cross-section, on which the gear is slidably disposed by virtue of a corresponding opening therein. The shaft may be for example a multi-spline shaft.

A further preferred feature of the invention provides that the receiving means is mounted movably in a vertical direction on a second slide means which is arranged on the first slide means and by which the above-mentioned vertical stroke and horizontal transportation movements of the slide means are transmitted to the receiving means during the regular testing mode of the apparatus, but by which, upon the receiving means encountering an obstacle during the downward movement thereof, further downward movement of the receiving means is prevented by a vertical relative movement between the receiving means and the first slide means. That contributes to substantially avoiding damage to the installation and/or a hollow body if a hollow body is in an inclined position, falls over, is of a contour which projects beyond the contour of the receiving means, or like situations. As the movement of the first slide means cannot be sufficiently quickly stopped in such a fault situation by virtue of the high level of mass inertia thereof and the high speeds involved, the relative movement along the second slide means when the receiving means is blocked ensures that the forces applied to the hollow body in that situation are limited. In this connection it is particularly advantageous if the relatively heavy synchronous motor is not arranged directly at the receiving means because that will accordingly reduce the mass inertia thereof. In the case of the receiving means being blocked as indicated above, it can further be provided that the apparatus is switched into a fault mode. The second slide means further affords the advantage of permitting simple adaptation to different types of hollow bodies such as bottles, as will be apparent from the following description of a preferred embodiment of the invention.

Finally, it can be provided that the predetermined angular amount through which the receiving means with the hollow body to be tested is rotated is 540° (one-and-a-half revolutions). That can ensure that further transportation movement of the hollow bodies occurs in a position comparable to that in which the hollow bodies were fed to the apparatus, or, when testing hollow bodies of a mirror-image symmetrical contour, in the same position. At the same time, that mode of operation permits complete detection of the transmission or reflection profiles over the entire angular region of the hollow body of 360°, without the need, in the evaluation procedure, to take account of the angular regions in which the rotary movement begins or is terminated, which makes it easier to evaluate the profiles involved.

Further objects, features and advantages of the present invention will be apparent from the following description of preferred embodiments thereof.

DESCRIPTION OF THE PREFERRED EMBODIMENTS

Figure 1:
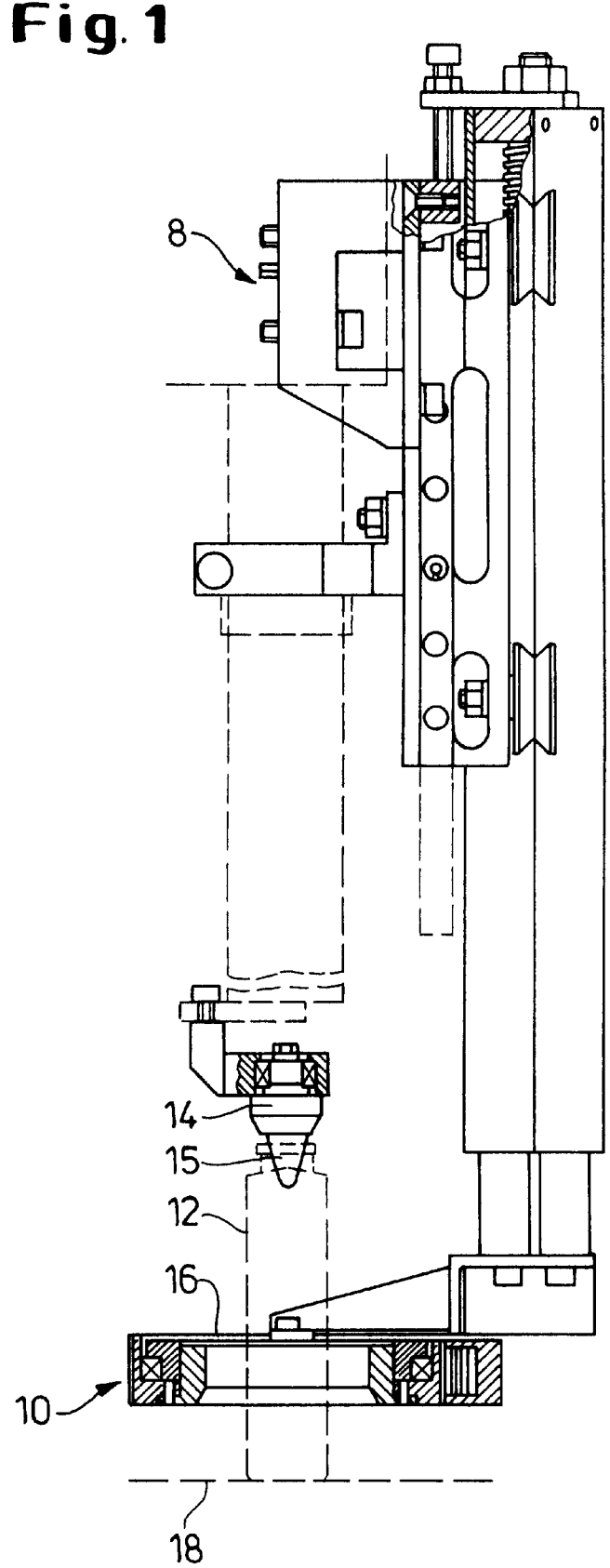
FIG. 1 is a diagrammatic side view of a testing apparatus in accordance with a first embodiment of the present invention.

Referring firstly to FIG. 1, reference numeral 8 therein generally identifies a lift stroke and transport arm with a receiving arrangement generally identified by reference numeral 10 for receiving a non-rotationally symmetrical hollow body to be tested for defects, illustrated in the form of a glass bottle 12, of a rectangular external contour. The arm 8 is moved over a substantially elliptical path of movement by way of an eccentric arrangement (not shown). In this respect, the mode of operation involved is as follows: the receiving arrangement 10 is lowered in position over the glass bottle 12 which is fed to the apparatus by a conveyor means in the form of a screw (not shown) and which is disposed in an upright position on a conveyor line such as a conveyor belt indicated at 18. The receiving arrangement 10 has a rotatably mounted receiving means 16 which is matched to the external contour of the glass bottle 12 in such a way that the receiving means 16 can embrace the bottle 12. Simultaneously with the receiving arrangement 10, a guidance means 14 having a guide bar portion 15 which is mounted in such a way as to be upwardly and downwardly movable is lowered into a position of engaging into the opening in the neck of the bottle 12, whereby the bottle 12 can additionally be stabilised in position on the conveyor belt 18. A suitable transmission such as a rack transmission in the mechanism of the arm 8 provides that the receiving means 16 is lowered twice as fast as the guidance means 14. The guidance means 14 and the receiving arrangement 10 provide for transportation movement of the bottle 12 through a test region of the apparatus, in a direction which is perpendicular to the plane of the drawing in FIG. 1. When that happens, at the same time there is a corresponding advance movement of the conveyor belt 18 in that direction. When a predetermined measurement position in the apparatus is reached the receiving means 16 which is adapted to be rotatable is rotated through a predetermined angular amount, preferably one-and-a-half revolutions (540°), about an axis which extends transversely with respect to the surface of the conveyor belt 18. During that rotary movement the optical transmission profile of the hollow body 12 to be tested for defects is recorded by a suitable measuring device at one or more heightwise levels of the hollow body or bottle 12, in dependence on the angle of rotary movement thereof. The rotary movement takes place so quickly that continuous further transportation movement of the bottle 12 does not substantially affect the measurement procedure. The operating movement of the arm 8 can be additionally slowed down while the measuring operation is being implemented, for example by a change in the travel range of the drive mechanism for the arm 8, for instance by suitably flattening off the profile of the eccentric of the driving eccentric arrangement producing the movement of the arm 8.

After the measurement procedure has been carried out the guidance means 14 and the receiving arrangement 10 are retracted upwardly from the bottle 12. The bottle 12 is then transported away out of the test region of the apparatus by way of the conveyor belt 18 and the arm 8 is moved back into its initial position, whereupon the above-described operating cycle is repeated.

Figure 2:
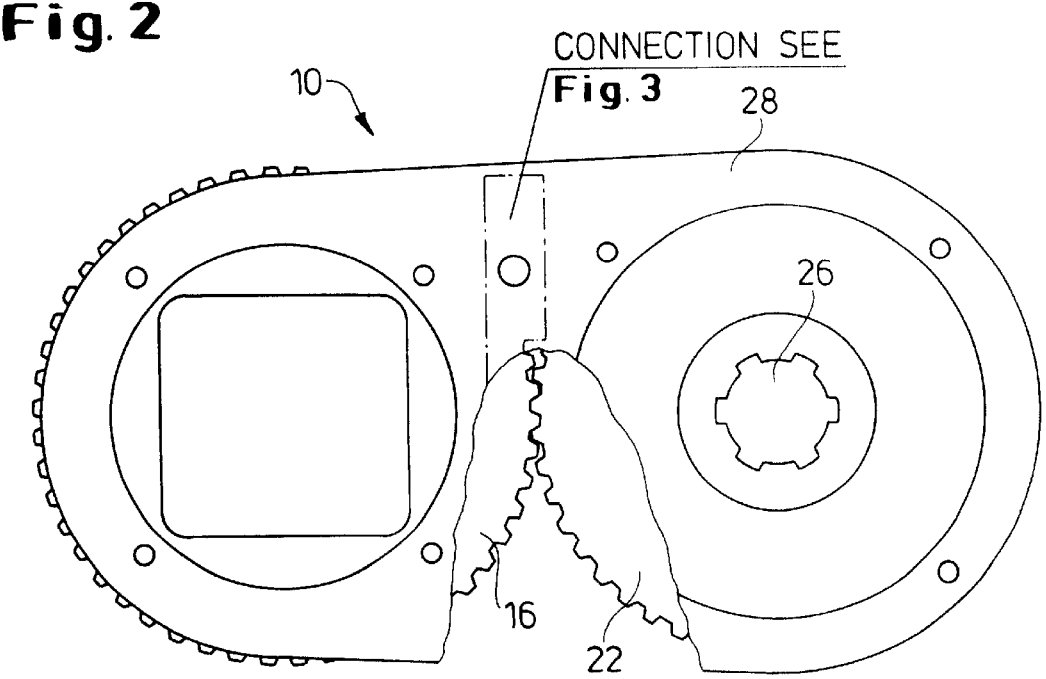
FIGS. 2 and 2A show a plan view and a side view respectively of a receiving arrangement in accordance with a preferred embodiment of the invention.
Figure 2A:
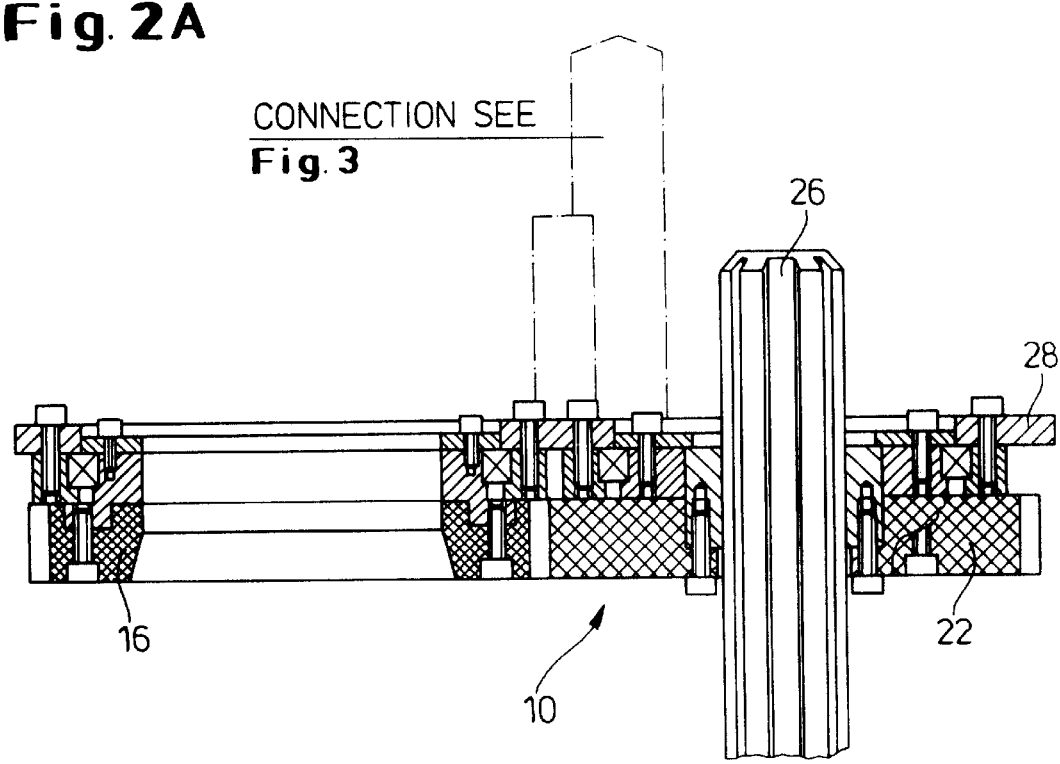

Referring now to FIGS. 2 and 2A, shown therein is a preferred embodiment of the receiving arrangement 10, which differs from the structure shown in FIG. 1 in the manner that will become apparent from the following description.

More specifically, the receiving arrangement 10 illustrated in FIGS. 2 and 2A has a carrier 28 which is rigidly connected to the lower part of the lifting stroke and transport arm 8. The actual receiving means 16 is rotatably mounted on the carrier 28. The receiving means 16 has an opening which is suitably matched to the respective contour of the non-rotationally symmetrical hollow bodies to be tested for defects, being rectangular in the present case, as shown in the upper part of the receiving arrangement 10 in FIG. 2. The receiving means 16 is adapted to be easily replaceable and interchangeable so as to permit conversion of the apparatus to a different type of hollow body, for example a different bottle configuration, in a short time. The receiving means 16 is supported on the carrier 28 by way of ring-type or annular bearings, as shown in FIG. 2A, preferably four-point thin-ring bearings.

The receiving means 16 further has an external tooth assembly which can be clearly seen in FIG. 2 and which engages into a gear indicated at 22 in FIG. 2. The gear 22 is also supported in relation to the carrier 28 by way of ring-type bearings and has a central opening of non-rotationally symmetrical cross-section for accommodating a shaft of corresponding cross-section, as indicated at 26, being in the form as illustrated of a multi-spline shaft, on which the gear 22 is axially slidable. The drive movement of a synchronous motor (not shown) of the apparatus is transmitted by way of the shaft 26 to the gear 22 and thus to the receiving means 16. The synchronous motor is arranged beneath the receiving arrangement 10 and does not participate in the upward and downward stroke movement of the receiving arrangement 10, but is constantly mechanically drivingly connected to the receiving arrangement 10 by way of the spline shaft 26.

The receiving arrangement 10 and the gear 22 are preferably made from plastic material.

Figure 3:
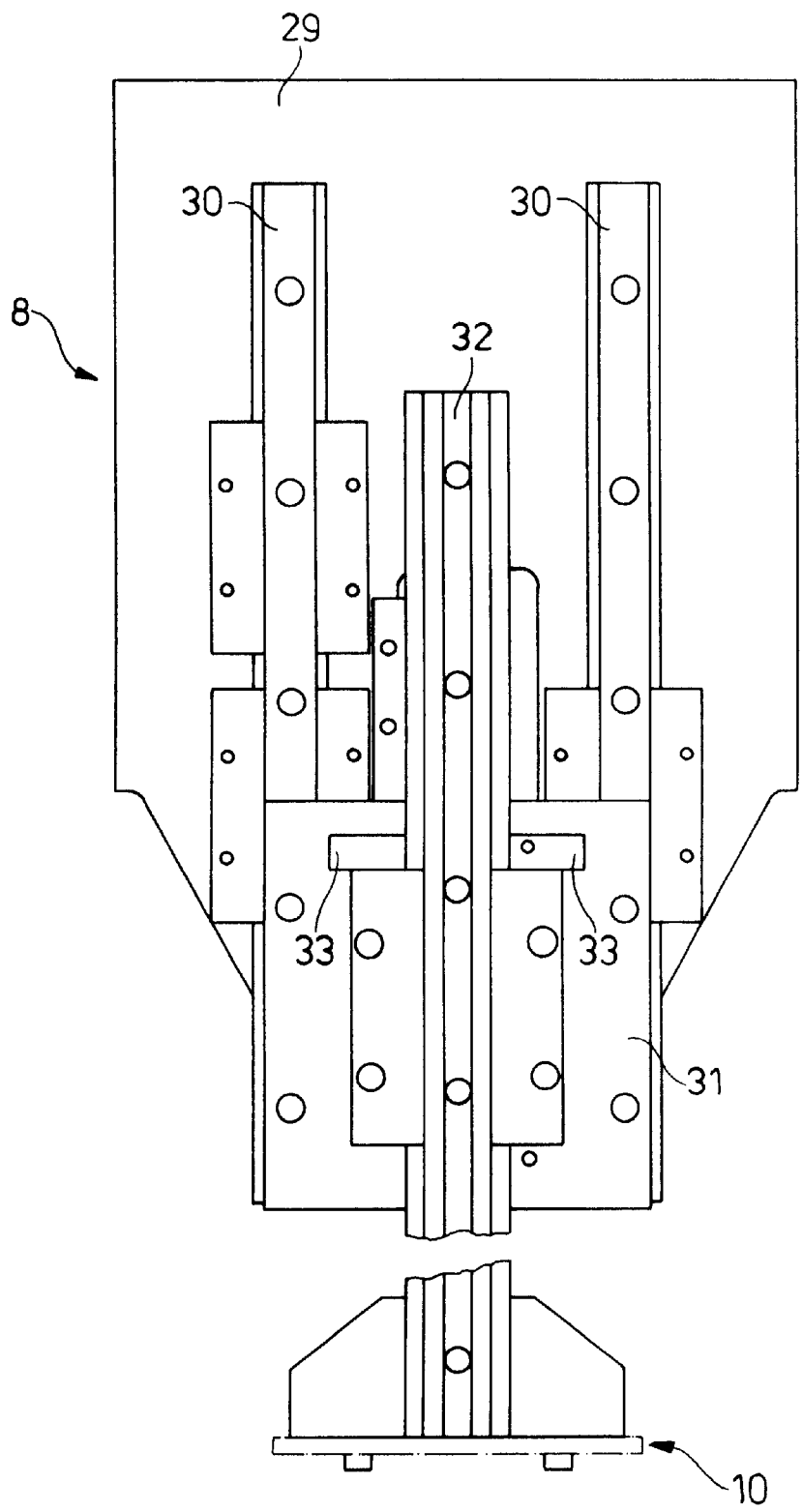
FIGS. 3 through 5 show views of a lift stroke and transportation arm in accordance with the preferred embodiment of the invention.
Figure 4:
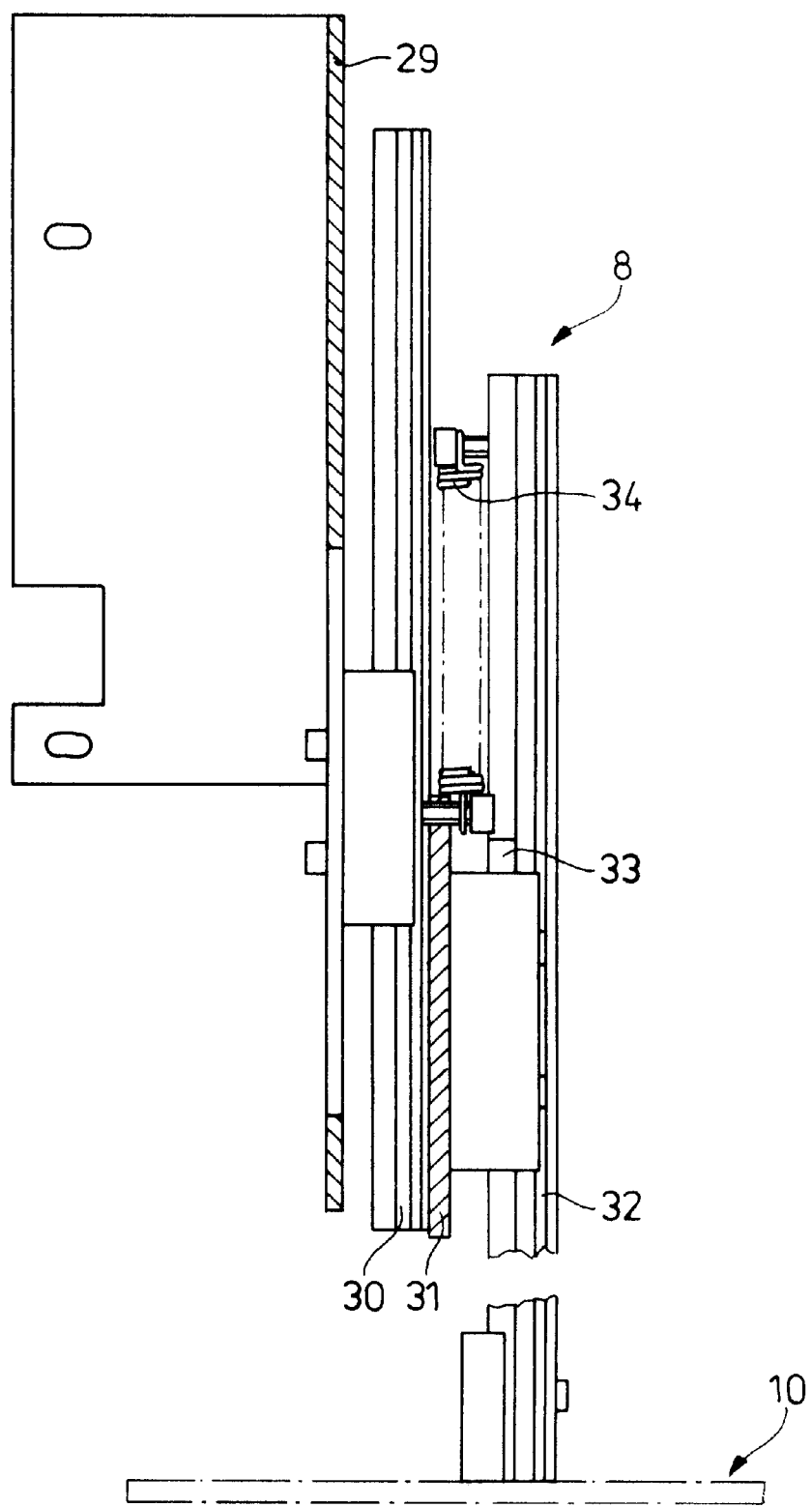
Figure 5:
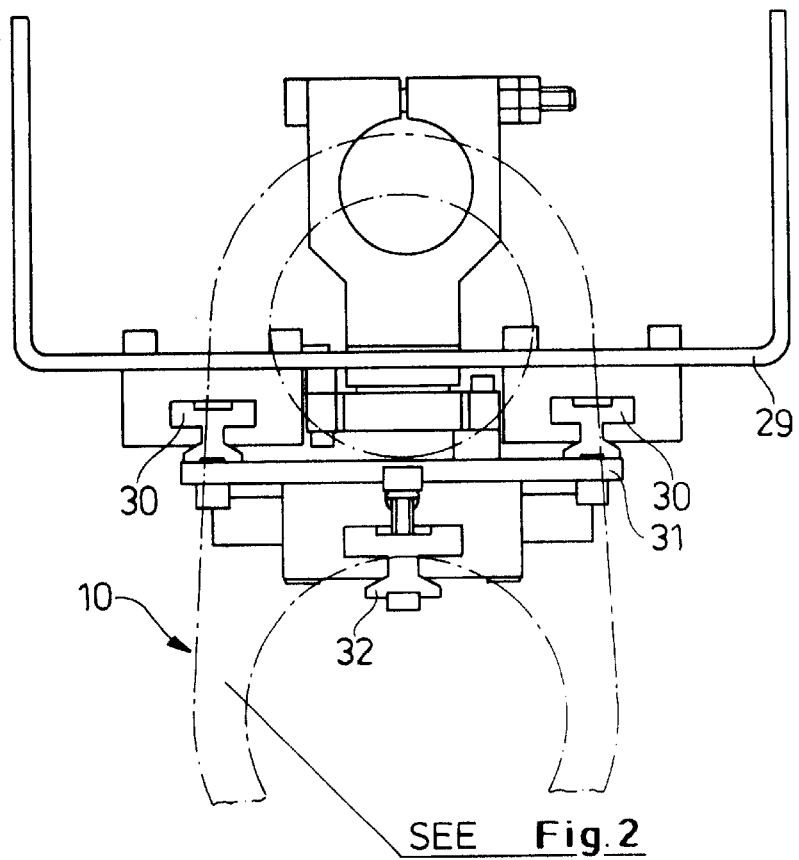

Reference will now be made to FIGS. 3 through 5 showing various views of the lift stroke and transport arrangement indicated generally at 8 in FIG. 1 and also indicated at 8 in the present Figures. The arrangement 8 is moved both in a horizontal direction, being a transport direction, and also in a vertical direction, referred to as the lift stroke direction, by way of a suitable eccentric drive arrangement. Guidance along the horizontal axis of movement is afforded by way of a first slide arrangement (not shown) on which an entire carrier 29 is horizontally displaced, in accordance with the eccentric movement. Arranged on the carrier 29 are guide slides in which a pair of rails 30 moves vertically with a slide 31 connected to the pair of rails 30. The slide 31 is pivotally connected to the eccentric arrangement (not shown).

A second slide 32 is vertically movably guided on the slide 31. The second slide 32 carries the receiving arrangement indicated at 10 in FIGS. 2 and 2A. When the apparatus is operating in the proper fashion for testing hollow bodies for defects, that is to say in the regular mode of testing operation thereof, the second slide 32 lies under the effect of the force of gravity with abutments 33 against the slide guides of the first slide 31 so that it moves together with the slide 31. If in a fault situation in the downward movement the receiving means 16 incorrectly encounters a hollow body such as a bottle which is for example not in the appropriate position or which is of the wrong configuration for the apparatus in its present settings, so that the receiving means 16 is blocked in its movement towards the hollow body, then the slide 31 can move with respect to the slide 32 so as to avoid damage to the apparatus structure and/or the hollow bodies being tested. The relative movement which occurs in that situation as between the slides 31 and 32 activates a spacing sensor (not shown) which causes the apparatus to be switched into a fault mode. In addition the height to which the receiving means 16 is lowered can be adjusted by virtue of displacement of the abutments 33 so that the apparatus can be quickly and easily adapted to deal with different types of hollow bodies or bottles.

Reference numeral 34 in FIG. 4 denotes a tension spring acting in the same direction as the force of gravity to eliminate undesirable relative movement as between the slides 31 and 32.

If the apparatus is to be used for testing bottles which involve a relatively low level of stability when standing up, for example the above-mentioned bottles of a wide rounded configuration for containing Franconian wine, then the illustrated embodiment may additionally have a guidance means 14 with a guide bar portion 15 as illustrated in the structure of FIG. 1.

Figure 6:
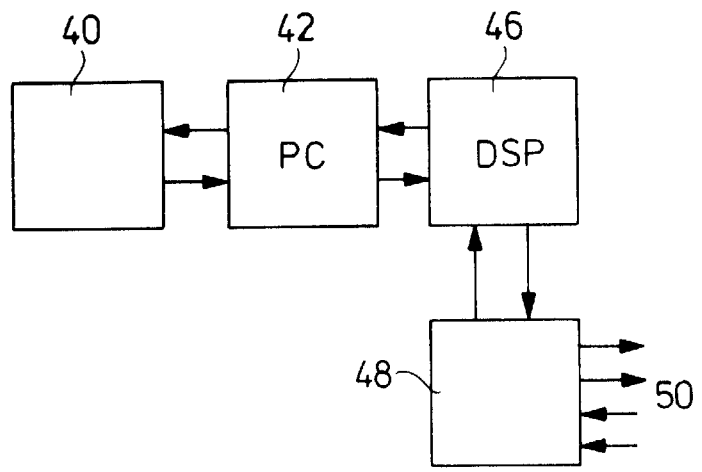
FIG. 6 shows a block circuit diagram of the electronic control system of a testing apparatus according to the present invention.

FIG. 6 shows a highly diagrammatic block circuit diagram illustrating the electronic control system of a testing apparatus in accordance with the present invention. The dialogue with an operator is implemented by way of a computer 42 in accordance with industry standard. The dialogue with theoperator is effected by way of a display screen, keyboard and mouse or trackball, which are generally identified by reference numeral 40. Acquisition of the sensor data and evaluation as to whether the hollow body being tested is a defective body is in contrast not effected by the computer 42 but by way of a signal processor 46 as it is only in that way that the required reaction times can be attained, by virtue of the fast cycle rates. The output and input signals of the signal processor are conditioned by means of a signal conditioning unit 48 in accordance with the demands of the respective sensors or actuators. The input and output signals 50 of the signal condtioning unit 48 include inter alia the current position of the drive eccentric for the arm 8, signals from one or more reflection/transmission sensors, a control signal for the synchronous motor, and a signal by means of which hollow bodies which are recognised as being defective are separated out.

It is found that the apparatus in accordance with the present invention permits extremely fast and reliable testing of non-rotationally symmetrical hollow bodies. A further advantage of the apparatus according to the invention is that the testing apparatus can be subsequently fitted, as a retro-fit device, to already existing machinery, at reasonable cost.

It will be appreciated that the above-described embodiments of the invention have been set forth solely by way of example and illustration of the principles thereof and that further modifications and alterations may be made therein without thereby departing from the spirit and scope of the invention.

What is claimed is:

1. Apparatus for testing non-rotationally symmetrical hollow bodies for defects, at least a part of the outer contour of each of the hollow bodies being non-round in shape, comprising
   a test region,
   a feed means for continuously conveying the hollow bodies into the test region, a means for conveying the hollow bodies through the test region, including receiving means adapted to embrace each of the hollow bodies and drive means adapted to move the receiving means over the respective hollow body to be tested which is supplied from said feed means, said receiving means having a receiving opening matched in shape to the outer contour of the hollow body to retain the hollow body in fixed relationship to the receiving means such that the hollow body is in a preselected axial orientation, a detector means at the test region for producing measurement values indicating the nature of the hollow body respectively being tested in dependence on an angle of rotation of the hollow body, the conveying means transporting the hollow body tested past the detector means, a means for rotating the receiving means with the hollow body retained therein through a predetermined angular amount during movement of the hollow body past the detector means, evaluation means for comparing the measurement values to predetermined values to determine whether the hollow body respectively being tested has defects, a means for conveying the hollow bodies out of the test region. and a means for removing the receiving means from the tested hollow body after the hollow body is moved out of the test region.

2. Apparatus as set forth in claim 1 including means for permitting replacement of said receiving means so that the receiving opening in the receiving means can be matched to the contour of the hollow bodies being tested.

3. Apparatus as set forth in claim 1 wherein the means for conveying the hollow bodies through the test region includes a guidance means comprising a guide bar portion which is centered with respect to the axis of rotation of the receiving means and means for moving said guide bar portion upwardly and downwardly, the guide bar portion being adapted to be introduced from above into a body opening the hollow body to be tested as the hollow body is being conveyed into the test region.

4. Apparatus as set forth in claim 1 wherein the receiving means has an axis of rotation and an external tooth means, and further including a first slide means, an eccentric means driving the first slide means to perform a stroke movement and a transport motion transverse with respect thereto, a gear operatively engaged with the external tooth means of the receiving means, and a synchronous motor operable to drive said gear.

5. Apparatus as set forth in claim 4 wherein said synchronous motor is disposed beneath the receiving means and is non-participatory in the stroke movement of said receiving means, said synchronous motor having a rotatable drive shaft, and further including a shaft of having a cross-section such that the gear is non-rotatably slidably mounted thereon, and means drivingly connecting the drive shaft of the motor to the shaft carrying the gear.

6. Apparatus as set forth in claim 5 including a second slide means on the first slide means, means mounting the receiving means movably in a vertical direction on the second slide means, whereby the stroke and transportation movement of the first slide means is transmitted to the receiving means during the regular testing mode but upon the receiving means encountering an obstacle during downward movement further downward movement of the receiving means is prevented by a vertical relative movement between the receiving means and the first slide means.

7. Apparatus as set forth in claim 1 wherein the predetermined angular amount through which the receiving means with the hollow body to be tested is rotated is 540°.

* * * * *